United States Patent [19]
Arlt et al.

[11] Patent Number: 4,986,884
[45] Date of Patent: Jan. 22, 1991

[54] PROCESS FOR THE PRODUCTION OF MONOMERIC α-CYANOACRYLATES

[75] Inventors: Wolfgang Arlt, Odenthal; Helmut Waniczek, Cologne; Richard Viard, Leverkusen; Dieter Brück, Cologne, all of Fed. Rep. of Germany

[73] Assignee: Bayer Aktiengesellschaft, Fed. Rep. of Germany

[21] Appl. No.: 113,648

[22] Filed: Oct. 28, 1987

[30] Foreign Application Priority Data

Nov. 8, 1986 [DE] Fed. Rep. of Germany ....... 3638171

[51] Int. Cl.$^5$ .......................... B01D 3/10; B01D 3/34; C07C 255/02
[52] U.S. Cl. .................. 203/8; 159/DIG. 8; 159/DIG. 16; 202/198; 202/205; 203/91; 558/443
[58] Field of Search .......................... 203/8, 90, 91, 87; 202/205, 198, 179, 236, 158; 159/DIG. 8, 48.1, DIG. 16; 558/443; 526/298

[56] References Cited

U.S. PATENT DOCUMENTS

| 2,763,585 | 9/1956 | Coover, Jr. et al. | 558/443 |
| 2,763,677 | 9/1956 | Jeremias | 526/298 |
| 2,776,232 | 1/1957 | Sheaver et al. | 558/443 |
| 3,465,027 | 9/1967 | Hawkins | 558/443 |
| 4,086,266 | 4/1978 | Corey | 558/443 |
| 4,170,585 | 10/1979 | Motegi et al. | 526/298 |
| 4,171,416 | 10/1979 | Motegi et al. | 526/298 |
| 4,364,876 | 12/1982 | Kimura et al. | 558/443 |
| 4,365,081 | 12/1982 | Shimizu et al. | 203/8 |
| 4,377,490 | 3/1983 | Shiraishi et al. | 526/210 |
| 4,386,193 | 5/1983 | Reich et al. | 526/209 |
| 4,425,471 | 1/1984 | Millet | 526/298 |
| 4,695,615 | 9/1987 | Leonard et al. | 526/209 |

FOREIGN PATENT DOCUMENTS

| 1568479 | 3/1970 | Fed. Rep. of Germany . | |
| 2231561 | 1/1974 | Fed. Rep. of Germany . | |
| 0097636 | 8/1979 | Japan | 558/443 |
| 2067553 | 7/1981 | United Kingdom | 558/443 |

Primary Examiner—Virginia Manoharan
Attorney, Agent, or Firm—Connolly & Hutz

[57] ABSTRACT

A process for the production of monomeric α-cyanoacrylates by pryrolysis of poly-α-cyanoacrylates and subsequent distillation of the resulting monomeric α-cyanoacrylates.

6 Claims, 2 Drawing Sheets

PROCESS FOR THE PRODUCTION OF MONOMERIC α-CYANOACRYLATES

This invention relates to a process for the production of α-cyanoacrylates by pyrolysis of poly-α-cyanoacrylates and subsequent distillation of the resulting monomeric α-cyanoacrylates.

It is known that monomeric α-cyanoacrylates polymerize very easily when they contain impurities. This lack of stability causes production difficulties and reduces the yields. In addition, monomeric α-cyanoacrylates show only very limited stability in storage even if they contain only small quantities of impurities which then adversely affects their useability, for example as adhesives. Accordingly, the monomeric α-cyanoacrylates formed in the pyrolysis of poly-α-cyanoacrylates have to be purified, for example by distillation.

Known distillation processes for the purification of monomeric α-cyanoacrylates are complicated and reduce the yields. In addition, the only known distillation processes comprise at most five separation stages in the distillation column (cf. for example DE-OS 2 231 561). With distillation processes of this type, high-purity α-cyanoacrylates can only be obtained when the distillation processes are carried out repeatedly. This results in a reduction in the yield of monomeric α-cyanoacrylate.

It has been found that pure, monomeric α-cyanoacrylates can actually be obtained in a single purification step providing they are distilled in countercurrent in the presence of polymerization inhibitors over more than ten separation stages.

The present invention relates to a process for the production of high-purity, monomeric α-cyanoacrylates by distillation under reduced pressure, characterized in that distillation is carried out in countercurrent at reduced pressure over more than ten separation stages, inhibitors are fed continuously to the countercurrent at the uppermost separation stage and stabilized, liquid α-cyanoacrylate is fed in at the places where condensate can collect.

According to the invention, the countercurrent may be produced in a countercurrent apparatus with a dephlegmator.

In the practical application of the invention, the interval between the individual separation stages is selected so that the next uppermost separation stage always lies in the spray range of the underlying separation stage. The dephlegmator or condenser projects into the spray range of the uppermost plate. At those places of the countercurrent apparatus where there is no danger of polymerization by virtue of the low concentration of α-cyanoacrylate, there is no need to supply stabilized liquid to the condensate, although this can be of advantage.

In the practical application of the process according to the invention, the countercurrent is produced in a countercurrent apparatus with a dephlegmator of which the operating temperature is selected so that impurities boiling below the α-cyanoacrylate can pass in the vapor phase while the α-cyanoacrylate is condensed. The temperature of the dephlegmator is selected so that it is below the boiling temperature of the α-cyanoacrylate, but more than 30° C. and preferably more than 50° C. above the boiling temperature of the alcohol on which the cyanoacrylate is based at the particular distillation pressure.

By α-cyanoacrylate are meant monomers corresponding to the following formula

in which R is a branched or unbranched, substituted or unsubstituted $C_1$–$C_{10}$ alkyl or cycloalkyl radical.

The countercurrent apparatus used in accordance with the invention is, for example, a plate column comprising 10 to 50 separation stages. A plate column comprising 20 to 50 separation stages is preferably used. The countercurrent apparatus is operated under reduced pressure, preferably under a pressure of from 5 to 100 mbar and more preferably under a pressure of from 10 to 50 mbar.

According to the invention, the return flow at one of the uppermost plates is divided into two parts, one of which is removed as the product stream while the other part is guided to the next lowest plate to produce the countercurrent.

At the uppermost separation stage, the countercurrent apparatus used in accordance with the invention comprises an opening with the possibility of continuously introducing one or more inhibitors either separately or together.

The inhibitors used prevent anionic polymerization and radical polymerization. In general, at least one anionic polymerization inhibitor and at least one radical polymerization inhibitor are introduced separately or together either as such or in solution.

It can be of advantage additionally to pass gaseous inhibitors, such as $SO_2$, through the countercurrent apparatus used in accordance with the invention during the distillation process.

According to the invention, it is only possible to use radical polymerization inhibitors which inhibit radical polymerization of the cyanoacrylate without initiating the anionic polymerization. For example, it is possible to use hydroquinone, pyrocatechol, resorcinol or derivatives thereof, such as hydroquinone monoethyl ether, or phenols, such as di-tert.-butylphenol or 2,6-di-tert.-butyl-p-cresol, 2,2'-methylene-bis-(4-methyl-6-tert.-butylphenol), bisphenol A, dihydroxydiphenylmethane, styrenized phenols.

The anionic polymerization inhibitors suitable for use in accordance with the invention suppress the anionic polymerization of the cyanoacrylates. For example, it is possible to use strong acids, Lewis acids, sulfuric acid, hydrochloric acid, sulfonic acids, such as methane, ethane or higher sulfonic acids, p-toluene sulfonic acid, phosphoric acid or polyphosphoric acids, silyl esters of strong acids, such as trialkyl chlorosilanes, dialkyl dichlorosilanes, alkyl trichlorosilanes, tetrachlorosilane, trialkyl silylsulfonic acids, trialkyl silyl-p-toluene sulfonates, bis-trialkyl silylsulfate and trialkyl silylphosphoric acid esters.

The radical polymerization inhibitors are fed in at the uppermost plate of the countercurrent apparatus used in accordance with the invention in such a quantity that the condensate flowing back from the dephlegmator, which thus forms the countercurrent, contains from 0.005 to 2% by weight inhibitor. An inhibitor content of from 0.01 to 1% by weight is preferred.

The radical polymerization or anionic polymerization inhibitors may be added individually or in admixture and at the same time or one after the other.

A stabilized α-cyanoacrylate is thus obtained as the distillation product. Accordingly, another advantage of the process according to the invention is that there is no longer any need for the otherwise difficult handling of unstabilized α-cyanoacrylate, nor is there any need for more stabilizers to be added.

According to the invention, the anionic polymerization inhibitors are fed in at the uppermost plate of the countercurrent apparatus in such a quantity that the countercurrent contains from 1 ppm to 100 ppm inhibitor, preferably from 5 ppm to 500 ppm inhibitor and more preferably from 10 ppm to 100 ppm inhibitor.

Since the inhibitors used in accordance with the invention may be solids, it can be of advantage to use them in the form of dilute solutions. Suitable solvents are branched or unbranched, aliphatic, cyclic or alicyclic, aromatic or araliphatic, substituted or unsubstituted hydrocarbons, such as n-hexane, n-heptane, n-octane, cyclopentane, cyclohexane, 2,2,4-trimethylpentane, benzene, toluene, chloroform or carbontetrachloride or cyanoacrylates. It can be an advantage if the solvents used are capable of forming azeotropes with water or alcohols.

The countercurrent apparatus used in accordance with the invention (see FIG. 1) is designed in such a way that stabilized α-cyanoacrylate is fed in at the places where condensate can collect. This may be achieved by arranging the separation stages at suitable intervals. The interval between two separation stages is shorter than the spray range of the lower separation stage. The dephlegmator projects into the spray range of the uppermost separation stage.

The dephlegmator is an apparatus above the uppermost separation stage. The vapors ascending in the countercurrent apparatus according to the invention are partially condensed in the dephlegmator so that a countercurrent is produced. The dephlegmator is operated at such a temperature that impurities boiling at a lower temperature than cyanoacrylate can pass in the vapor phase while the cyanoacrylate is condensed.

The operating temperature of the dephlegmator ($T_{Deph}$) is selected in dependence upon the particular distillation pressure of 5 to 100 mbar. This temperature is selected so that it is below the boiling temperature ($T_1$) of the α-cyanoacrylate at the distillation pressure applied, but above the boiling temperature ($T_2$) of the alcohol on which the α-cyanoacrylate is based at the particular distillation pressure applied. The dephlegmator temperature ($T_{Deph}$) is $$(T_2) < (T_{Deph}) < (T_1),$$

preferably $$(T_2 + 30° C.) < (T_{Deph}) < (T_1 - 10° C.)$$

and, more preferably, $$(T_2 + 40° C.) < (T_{Deph}) < (T_1 - 25° C.).$$

In the process according to the invention, the high-purity α-cyanoacrylate is run off as liquid phase in a side stream from one of the upper plates of the countercurrent apparatus. The α-cyanoacrylate is preferably run off from one of the eight uppermost plates.

The high-purity α-cyanoacrylates prepared in accordance with the invention are suitable for use as quick-setting, storable adhesives. Standard additives, polymers, dyes or stabilizers may be added to them in order to adjust certain properties, such as viscosity, color or setting rate.

Figure 1:
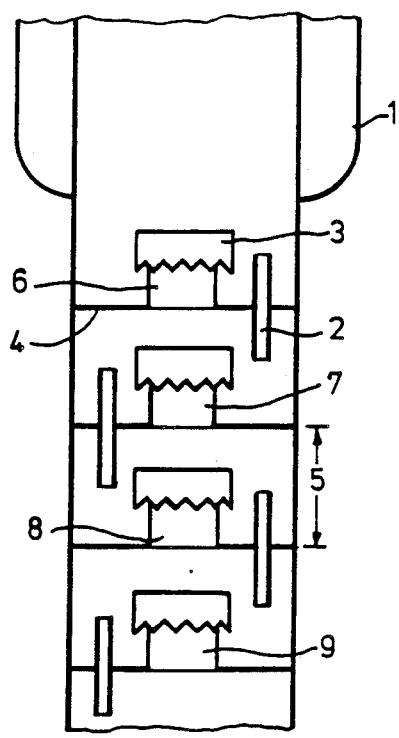
FIGS. 1 and 2 are diagrammatical views of the apparatus for carrying out the distillation process of the present invention.
Figure 2:
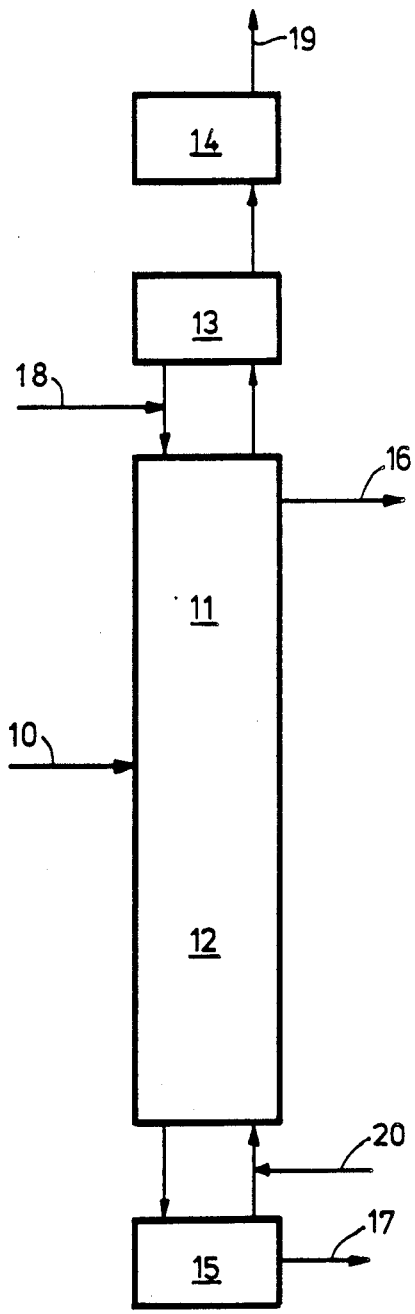

The distillation apparatus shown in FIGS. 1 and 2 may be used to carry out the distillation process according to the invention.

FIG. 1 shows a bubble plate column of the concentrating column in which:

1 = cooling jacket of the dephlegmator (situated in the spray range of the bubble cap 6),
2 = outlet duct,
3 = uppermost bubble cap,
4 = underneath of the bubble plate (situated in the spray range of the bubble cap 7),
5 = spray range of the bubble caps,
6,7,8,9 = bubble caps.

One possible arrangement for carrying out the distillation process according to the invention is shown in FIG. 2. 11 is the concentrating column and 12 the separation column of a distillation column. The mixture to be separated flows into this column in the form of the stream 10. The stream 18 consists of the inhibitors required for carrying out the process according to the invention which are combined with the stream of liquid coming from the dephlegmator 13. The vapors which are not condensed in the dephlegmator, more especially the gaseous inhibitor, or low-boiling components are liquefied in a supercooled condenser 14 and discarded. The condenser is connected via the outlet 19 to a vacuum unit.

The product vapor required for operating the distillation column is produced in the evaporator 15 which enables the sump product to be carefully evaporated by virtue of its particular construction (minimal temperature stressing and residence time). The sump product leaves the distillation column in the form of the stream 17. Gaseous inhibitors may be introduced into the column in the form of the stream 20.

The stream 16 is the outlet for pure product situated a few separation stages beneath the dephlegmator. Pure product is removed as liquid in only such a regulated quantity that the stream flowing downwards through the concentrating column is just sufficient for product separation.

EXAMPLES

A laboratory distillation column constructed on the principle illustrated in FIGS. 1 and 2 had 20 bubble plates in the separating column and 23 bubble plates without any intermediate plates in the concentrating column. The product stream 16 was run off as liquid at the third plate beneath the dephlegmator. The removal rate was adjusted in such a way that the ratio between the quantity removed and the quantity continuing to flow through the concentrating column was 1 : 4. The dephlegmator was operated at 45° C. and was situated in the spray range of the uppermost plate. The sump evaporator 15 was a falling-film evaporator. The distillation column was operated at a head pressure of 20 mbar. The following product streams were established or reached:

Stream 10 (feed): 273 g/h
86.1% ethyl cyanoacrylate (technical quality)
3.9% secondary products
Stream 18 (inhibitor feed): 19.6 g/h
0.03% bis-trimethyl silylsulfate
1.0% Vulkanox-BKF ®, a product of Bayer AG (2,2'-methylene-bis-(4-methyl-6-tert.-butylphenol)) in n-hexane
Stream 16 (pure product removable): 219.2 g/h
<99.5% ethyl cyanoacrylate
0.5% other products
Stream 17 (sump removal): 29.9 g/h
100% high-boiling secondary components 44 g low-boiling fractions were distilled off in the supercooler 14 after a distillation time of 1 hour. Even after several weeks' distillation, there was still no indication of polymerization.

Definitions of terms used

Separation stage

In a countercurrent apparatus, a separation stage leads to an exchange of mass and energy and hence to a change in the streams. In the distillation field, a separation stage corresponds to the plate of a plate column or to a certain packing height in a packed column.

Condensate

In the context of the invention, condensate is understood to be the liquid condensing from the vapor phase (for example on relatively cold walls on the next uppermost plate) which shows a tendency towards polymerization on account of its cyanoacrylate content and the absence of the liquid inhibitors.

Return flow divider

In a countercurrent distillation column, a stream of liquid flows downwards and a stream of vapor upwards. The stream of vapor is essentially determined by the heat applied to the bottom of the column while the stream of liquid is essentially determined by the division of the condensate of the condenser or dephlegmator into the product stream and the return stream. This function is performed by the return flow divider.

We claim:

1. A process for the purification of monomeric α-cyanoacrylates comprising the steps of utilizing a countercurrent distillation apparatus having more than ten separation stages and a dephlegmator, introducing monomeric α-cyanoacrylates into the apparatus, distilling the monomeric α-cyanoacrylates under reduced pressure of from 5 to 100 mbar, carrying out the distillation over more than ten separation stages, continuously introducing inhibitors into the countercurrent distillation apparatus at the upper separation stage, and feeding liquid α-cyanoacrylate into the distillation apparatus at those places where condensate is collected.

2. A process as claimed in claim 1 including the step of removing liquid α-cyanoacrylate from one of eight uppermost stages, counting from the dephlegmator.

3. A process as claimed in claim 1 wherein the dephlegmator temperature ($T_{Deph}$) satisfies condition $(T_2) < (T_{Deph}) < (T_1)$ wherein $T_1$ is the boiling temperature of the α-cyanoacrylate at the distillation temperature applied and $T_2$ is the boiling temperature of alcohol on which the α-cyanoacrylate is based at the distillation pressure applied.

4. A process as claimed in claim 1 wherein the condensate produced in the dephlegmator is stabilized with from 0.005 to 25 by weight radical polymerization inhibitors and with from 1 to 1000 ppm anionic polymerization inhibitors.

5. A process as claimed in claim 1 wherein the separation stages include a spray range and the dephlegmator extends into the spray range of the uppermost separation stage.

6. A process as claimed in claim 1 wherein the separation stages include a spray range and the interval between the separation stages is selected so that the next uppermost separation stage lies in the spray range of the underlying separation stage.

* * * * *

UNITED STATES PATENT AND TRADEMARK OFFICE
CERTIFICATE OF CORRECTION

PATENT NO. : 4,986,884
DATED : Januar 22, 1991
INVENTOR(S) : Wolfgang Arlt et al It is certified that error appears in the above-identified patent and that said Letters Patent is hereby corrected as shown below:

Column 3, line 13, "100" should read -- 1000 --.

Column 5, line 5, "3.9%" should read -- 13.9% --.

Column 5, line 13, "0.5%" should read -- > 0.5% --.

Signed and Sealed this

Twentieth Day of October, 1992

Attest:

DOUGLAS B. COMER

*Attesting Officer*         *Acting Commissioner of Patents and Trademarks*